United States Patent [19]

Friebe et al.

[11] 4,212,866
[45] Jul. 15, 1980

[54] PHARMACEUTICALLY ACTIVE DERIVATIVES OF 9-[3-(4-AMINO-PIPERIDINO)-PROPYL]-ADENINES

[75] Inventors: Walter-Gunar Friebe, Darmstadt; Max Thiel, Mannheim; Androniki Roesch, Mannheim; Otto-Henning Wilhelms, Heddesheim; Wolfgang Schaumann, Heidelberg, all of Fed. Rep. of Germany

[73] Assignee: Boehringer Mannheim GmbH, Mannheim, Fed. Rep. of Germany

[21] Appl. No.: 6,050

[22] Filed: Jan. 24, 1979

[30] Foreign Application Priority Data

Feb. 2, 1978 [DE] Fed. Rep. of Germany ....... 2804168

[51] Int. Cl.$^2$ ............................................. C07D 473/00
[52] U.S. Cl. ....................................... 424/253; 544/277
[58] Field of Search ......................... 544/277; 424/253

[56] References Cited

U.S. PATENT DOCUMENTS

| | | | |
|---|---|---|---|
| 3,917,596 | 11/1975 | Winter et al. | 544/277 |
| 3,996,361 | 12/1976 | Friebe | 544/277 |
| 4,086,347 | 4/1978 | Friebe et al. | 544/277 |

Primary Examiner—Nicholas S. Rizzo

Attorney, Agent, or Firm—Sprung, Felfe, Horn, Lynch & Kramer

[57] ABSTRACT

Novel 9-[3-(4-amino-piperidino)-propyl]-adenine derivatives of the formula

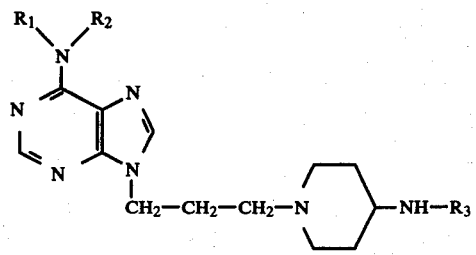

wherein
$R_1$ is a hydrogen atom or a lower alkyl radical,
$R_2$ is a hydrogen atom, an aryl radical, a lower alkyl radical, a hydroxy lower alkyl radical, or together with $R_1$ and the nitrogen atom to which they are attached form a heterocyclic ring, and
$R_3$ is a hydrogen atom or an acyl radical, or salts thereof with pharmacologically acceptable acids, characterized by anti-allergic, anti-inflammatory and anti-oedematous activity.

14 Claims, No Drawings

PHARMACEUTICALLY ACTIVE DERIVATIVES OF 9-[3-(4-AMINO-PIPERIDINO)-PROPYL]-ADENINES

The present invention is concerned with new purine derivatives, with the preparation thereof and with pharmaceutical compositions containing them.

U.S. Pat. No. 4,086,347 describes purine derivatives with antiallergic, anti-inflammatory, anti-oedematous and anti-hypertensive action, these compounds having a piperidinopropyl radical in the 9-position, the 4-position of the piperidine moiety being substituted by a phenoxymethyl radical.

We have now found that analogous purine derivatives, the 4-position of the piperidine moiety of which is substituted by an optionally acylated amino group, also have anti-allergic, anti-inflammatory and anti-oedematous activities.

Thus, according to the present invention, there are provided piperidinoalkyl derivatives of purine of the general formula:

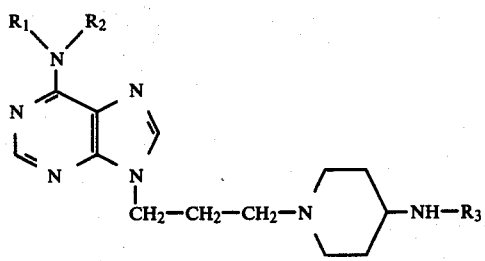
(I)

wherein $R_1$ is a hydrogen atom or a lower alkyl radical, $R_2$ is a hydrogen atom, an aryl or a lower alkyl radical which is optionally substituted by hydroxyl or $R_1$ and $R_2$, together with the nitrogen atom to which they are attached, can also form a heterocyclic ring and $R_3$ is a hydrogen atom or an acyl radical; and the salts thereof with pharmacologically acceptable acids.

When $R_1$ and $R_2$, together with the nitrogen atom to which they are attached, represent a heterocyclic ring, then this ring can be, for example, a tetramethyleneimino, pentamethyleneimino or hexamethyleneimino ring.

The acyl radicals of the substituents $R_3$ can be lower alkanoyl radicals which are optionally substituted one or more times by halogen atoms and/or by aryl radicals; or aryl-substituted lower alkenoyl radicals, for example, the cinnamoyl or 3,4-dimethoxycinnamoyl radical; or carbocyclic or heterocyclic aroyl radicals, which are optionally substituted by halogen atoms, hydroxyl, lower alkyl, lower alkoxy, lower alkoxycarbonyl, lower acyloxy, carboxyl, nitro, amino, cyano, trifluoromethyl, carbamoyl or benzyl.

Heterocyclic aroyl radicals can be, for example, the furanecarbonyl, thiophenecarbonyl or pyridine-carbonyl radicals and the carbocyclic aroyl radical can be, for example, a benzoyl radical.

Furthermore, $R_3$ can be the acidic residue of a cycloalkylcarboxylic acid, the cycloalkyl moiety preferably being a cyclopropyl, cyclobutyl, cyclopentyl, cyclohexyl or cyclohaptyl radical.

Furthermore, when $R_3$ is an acyl radical, this can also be an acidic residue derived from a sulphonic acid, for example, benzenesulphonic acid or methylsulphonic acid.

The expression "aryl" in the definitions of the substituents $R_2$ and $R_3$ preferably means, in all cases, a phenyl or naphthyl radical. The lower alkyl, lower alkoxy or lower alkanoyl moieties of $R_1, R_2$ or $R_3$ can be straight-chained or branched and contain up to 6 and preferably up to 4 carbon atoms.

The halogen atoms are fluorine, chlorine or bromine atoms.

Apart from the compounds mentioned hereinafter in the specific examples, the present invention also includes, in particular, all compounds which have every possible combination of the substituents mentioned in the specific examples.

We have found that the new compounds of general formula (I) suppress the liberation and the action of histamine and can thus have anti-allergic, anti-inflammatory and anti-oedematous activities.

The new compounds of general formula (I) according to the present invention can be prepared, for example, by reacting a compound of the general formula:

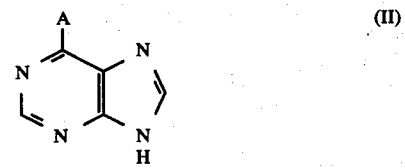
(II)

wherein A is a reactive residue or an

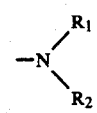

radical, $R_1$ and $R_2$ having the same meanings as above, with a compound of the general formula:

X—CH$_2$—CH$_2$—CH$_2$—Y (III), wherein X and Y are reactive residues, and with a compound of the general formula:

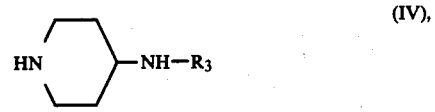
(IV), wherein $R_3$ has the same meaning as above, whereby, when A signifies a reactive group, the

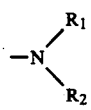

radical must be subsequently introduced, subsequently, if desired, the $R_3$ group is replaced by a different $R_3$ group by saponification and subsequent acylation with a compound of the general formula $R_3$-Z, wherein Z is a reactive residue, and, if desired, a nitro group is subsequently converted into an amino group by hydrogenation and subsequently, if desired, the reaction product obtained is converted into a pharmacologically acceptable salt.

The reactive residues X and Y in the compounds of general formula (III) can be, for example, chlorine or bromine atoms or mesyloxy or tosyloxy radicals. The reactive residue A in compounds of general formula (II) is to be understood to be a halogen atom, preferably a chlorine or bromine atom, or an alkylthio or benzylthio radical.

Reactive residues Z can be all residues which are used in peptide chemistry for the activation of carboxylic acid, for example halogen atoms, the azido group and alkoxy, aryloxy and acyloxy radicals.

The process according to the present invention is preferably carried out by first condensing a compound of general formula (III) with a compound of the general formula (IV), the reaction product formed being isolated. This intermediate is then reacted with a compound of general formula (II). The reaction is preferably carried out in an alkaline medium and especially in a lower alcohol, for example isopropanol, in the presence of sodium isopropanolate. Under these conditions, compounds are obtained of general formula (I), as well as small amounts of isomeric derivatives which are substituted in the 7-position but which can, however, be removed from the desired reaction products by recrystallization (via 9-substitution of the adenine in an alkaline medium; cf. also "The Chemistry of heterocyclic compounds": Fused pyrimidines, Part II, Purines, pub. Wiley-Interscience, page 342).

According to another variant, a compound of general formula (II) is first reacted with a compound of general formula (III). Subsequently, the reaction mixture obtained is reacted with a compound of general formula (IV) to give a desired end product of general formula (I).

When A is a reactive group, then the

radical must be subsequently introduced. This can take place by processes which are well known in the field of purine chemistry (cf. loc. cit., page 159).

A subsequent conversion of an $R_3$ group in a compound of general formula (I) into a different $R_3$ group preferably takes place by the exchange of one acyl radical $R_3$ by a different radical $R_3$. For this purpose, compounds of general formula (I) are first saponified in an acidic medium and the intermediate products obtained are preferably acylated in the presence of an acid-binding agent in known manner. The 9-[3-(4-aminopiperidino)-propyl]-adenine derivatives obtained as intermediates are also new compounds.

Furthermore, in a compound of general formula (I) in which the acyl radical $R_3$ contains a nitro group, the nitro group can be converted in known manner into an amino group, for example by catalytic hydrogenation.

Compounds of general formulae (II), (III) and (IV) are known from the literature and can easily be prepared from known compounds by means of well-known methods.

Compounds of general formula (IV) can be prepared in known manner, for example by appropriately acylating a 4-aminopiperidine which has a protective group on the cyclic nitrogen atom, followed by splitting off the protective group.

The pharmacologically acceptable salts can be obtained in the usual manner, for example by neutralization of the compounds of general formula (I) with non-toxic inorganic or organic acids, for example, hydrochloric acid, sulphuric acid, phosphoric acid, hydrobromic acid, acetic acid, lactic acid, citric acid, malic acid, salicyclic acid, malonic acid, maleic acid or succinic acid.

The new compounds of general formula (I) according to the present invention and the salts thereof can be administered enterally and parenterally in admixture with liquid or solid pharmaceutical diluents or carriers. In this case, there can be used all the conventional forms of administration, for example tablets, capsules, dragees, syrups, solutions, suspensions and the like. As injection medium, it is preferable to use water which contains the usual additives for injection solutions, for example stabilizing agents, solubilizing agents and/or buffers. Additives of this type include, for example, tartrate and citrate buffers, ethanol, complex-forming agents (such as ethylenediamine-tetraacetic acid and the non-toxic salts thereof) and high molecular weight polymers (such as liquid polyethylene oxide). Liquid carrier materials for injection solutions must be sterile and are preferably placed into ampules. Solid carrier materials can be, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions which are suitable for oral administration can, if desired, contain flavoring and sweetening agents.

Preferred compounds according to the present invention are, apart from those mentioned in the following examples, also the following compounds:

9-{3-[4-(2-chlorobenzamido)-piperidino]-propyl}-adenine

9-{3-[4-(3-chlorobenzamido)-piperidino]-propyl}-adenine

9-{3-[4-(3-methoxy-benzamido)-piperidino]-propyl}-adenine

9-{3-[4-(4-methoxy-benzamido)-piperidino]-propyl}-adenine

9-{3-[4-(2-acetoxy-benzamido)-piperidino]-propyl}-adenine

9-{3-[4-(3-methyl-benzamido)-piperidino]-propyl}-adenine

9-{3-[4-(4-benzyl-benzamido)-piperidino]-propyl}-adenine

9-{3-[4-(4-cyano-benzamido)-piperidino]-propyl}-adenine

9-{3-[4-(4-ethoxycarbonyl-benzamido)-piperidino]-propyl}-adenine.

9-{3-[4-(4-carboxy-benzamido)-piperidino]-propyl}-adenine $N^6$-ethyl-9-[3-(4-benzamido-piperidino)-propyl]-adenine $N^6$-phenyl-9-[3-(4-benzamido-piperidino)-propyl]-adenine 6-pyrrolidino-9-[3-(4-benzamido-piperidino)-propyl]-purine 9-[3-(4-trifluoroacetamido-piperidino)-propyl]-adenine 9-[3-(4-butyramido-piperidino)-propyl]-adenine and 9-[3-(4-cyclopentanearbonylamido-piperidino)-propyl]-adenine, as well as their salts with pharmacologically acceptable acids.

The following examples are given for the purpose of illustrating the present invention:

EXAMPLE 1

9-[3-(4-Benzamido-piperidino)-propyl]-adenine 4.7 g. (0.035 mole) Adenine are added to a solution of 0.8 g. (0.035 mole) sodium in 125 ml. isopropanol, heated under reflux for 10 minutes and then 11.2 g. (0.04 mole) 3-(4-benzamido-piperidino)-propyl chloride in 50 ml. isopropanol added thereto. After stirring the reaction mixture for 6 hours under reflux, it is evaporated in a vacuum. The residue is taken up in methylene chloride, the solution is washed with aqueous 2 N sodium hydroxide solution and subsequently with water, evaporated and the residue recrystallized from ethanol. There are obtained 7.1 g. (54% of theory) 9-[3-(4-benzamido-piperidino)-propyl]-adenine; m.p. 213°–214° C.

The 3-(4-benzamido-piperidino)-propyl chloride used as reaction component is prepared as follows:

A mixture of 20.4 g. (0.1 mole) 4-benzamido-piperidine, 15.7 g. (0.1 mole) 1-bromo-3-chloropropane, 30.3 g. (0.3 mole) triethylamine and 200 ml. tetrahydrofuran is heated under reflux for 6 hours and filtered. The filtrate is evaporated in a vacuum, the residue is extracted with ethyl acetate and the extract is evaporated. There are obtained 13.0 g. (46.5% of theory) 3-(4-benzamido-piperidino)-propyl chloride; m.p. 128°–130° C.

The substituted acylaminopiperidinopropyl chlorides used in the following examples are prepared in a corresponding manner.

EXAMPLE 2

The following compounds are obtained in a manner analogous to that described in Example 1:

| | Product | Yield % | m.p. (solvent used for recrystallization) |
|---|---|---|---|
| (a) | 9-{3-[4-(2-Fluorobenzamido)-piperidino]-propyl}-adenine from adenine and 3-[4-(2-fluorobenzamido)-piperidino]-propyl chloride | 50 | 180–181 (isopropanol) |
| (b) | 9-{3-[4-(4-Fluorobenzamido)-piperidino]-propyl}-adenine from adenine and 3-[4-(4-fluorobenzamido)-piperidino]-propyl chloride | 46 | 203–204 (isopropanol) |
| (c) | 9-{3-[4-(2-Methoxy-benzamido)-piperidino]-propyl}-adenine from adenine and 3-[4-(2-methoxy benzamido)-piperidio]-propyl chloride | 66 | 139–141 (diethyl ether) |
| (d) | 9-{3-[4-(n-Butoxy-benzamido)-piperidino]-propyl}-adenine from adenine and 3-[4-(4-n-butoxy benzamido)-piperidino]-propyl chloride | 32 | 208–210 (isopropanol) |
| (e) | 9-{3-[4-(2-Methyl-benzamido)-piperidino]-propyl}-adenine from adenine and 3-[4-(2-methyl-benzamido)-piperidino]-propyl chloride | 35 | 182–183 (isopropanol) |
| (f) | 9-{-[4-(4-Methyl-benzamido)-piperidio]-propyl}-adenine from adenine and 3-[4-(4-methyl-benzamido)-piperidino]-propyl chloride | 25 | 220–222 (isopropanol) |
| (g) | 9-{3-[4-(3-Trifluoromethyl-benzamido)-piperidino]-propyl}-adenine from adenine and 3-[4-(3-Trifluoromethyl-benzamido)-piperidino]-propyl chloride | 39 | 176–177 (ethyl acetate) |
| (h) | 9-{3-[4-(4-t-Butyl-benzamido)-piperidino]-propyl}-adenine from adenine and 3-[4-(4-t-butyl-benzamido)-piperidino]-propyl chloride | 49 | 185–187 (diethyl ether) |
| (i) | $N^6$-Methyl-9-[3-(4-benzamido-piperidino)-propyl]-adenine from $N^6$-methyladenine and 3-(4-benzamido-piperidino)-propyl chloride | 31 | 212–214 (isopropanol/diethyl ether) |
| (j) | $N^6$-(2-Hydroxyethyl)-9-[3-(4-benzamido-piperidino)-propyl] adenine from $N^6$-(2-hydroxyethyl)-adenine and 3-(4-benzamido-piperidino)-propyl chloride | 46 | 154–155 (isopropanol) |
| (k) | $N^6$-n-Butyl-9-[3-(4-Benzamido-piperidino)-propyl]-adenine from $N^6$-n-butyladenine and 3-(4-benzamido-piperidino)-propyl chloride | 46 | 190–192 (isopropanol/diethyl ether) |
| (l) | 6-Dimethylamino-9-[3-(4-benzamido-piperidino)-propyl]-purine from 6-dimethylamio-purine and 3-(4-benzamido-piperidino)-propyl chloride | 61 | 105–107 (ethyl acetate/diethyl ether) |
| (m) | 6-Piperidino-9-[3-(4-benzamido-piperidino)-propyl]-purine from 6-piperidino-purine and 3-(4-benzamido-piperidino)-propyl chloride | 69 | 144–145 (isopropanol) |
| (n) | 9-[3-(4-Acetamido-piperidino)-propyl]-adenine from adenine and 3-(4-acetamido-piperidino)-propyl chloride | 34 | 213–215 (isopropanol/diethyl ether) |

EXAMPLE 3

9-[3-(4-Cinnamoylamido-piperidino)-propyl]-adenine 3.7 g. (0.022 mole) Cinnamoyl chloride are added dropwise to a mixture of 6.2 g. (0.02 mole) 9-[3-(4-aminopiperidino)-propyl]-adenine and 100 ml. 1 N aqueous sodium hydroxide solution. The reaction mixture is stirred for 5 hours at ambient temperature, filtered and recrystallized from isopropanol. There are obtained 3.2 g. (39% of theory) 9-[3-(4-cinnamoylamido-piperidino)-propyl]-adenine; m.p. 217°–219° C.

The 9-[3-(4-aminopiperidino)-propyl]-adenine used as reaction component can be prepared as follows:

A mixture of 32.0 g. (0.085 mole) 9-[3-(4-benzamido-piperidino)-propyl]-adenine and 500 ml. 5 N hydrochloric acid is heated under reflux for 6 hours. The reaction mixture is allowed to cool, washed with diethyl ether, rendered alkaline, extracted with methylene chloride and the extract evaporated. After recrystallization of the residue from isopropanol, there are obtained 14.6 g. 9-[3-(4-aminopiperidino)-propyl]-adenine (62% of theory); m.p. 140°–142° C. The corresponding hydrochloride melts at 318°–320° C.

EXAMPLE 4

The following compounds are obtained in a manner analogous to that described in Example 3:

| | Product | Yield | m.p. (solvent used for recrystallization) |
|---|---|---|---|
| (a) | 9-{3-[4-(4-Chlorobenzamido)-piperidino]-propyl}-adenine from 9-[3-(4-amino-piperidino)-propyl]-adenine and 4-chlorobenzoyl chloride | 41 | 203–205 (isopropanol/diethyl ether) |
| (b) | 9-{3-[4-(2-Hydroxy-benzamido)-piperidino]-propyl}-adenine from 9-[3-(4-amino-piperidino)-propyl]-adenine and salicylyl chloride | 19 | 193–195 (acetone) |
| (c) | 9-{3-[4-(4-Nitro-benzamido)-piperidino]-propyl}-adenine from 9-[3-(4-amino-piperidino)-propyl]-adenine and 4-nitro-benzoyl chloride | 28 | 142–143 (isopropanol) |
| (d) | 9-{3-[4-(Phenyl-acetamido)-piperidino]-propyl}-adenine from 9-[3-(4-amino-piperidino)-propyl]-adenine and phenylacetyl chloride | 32 | 190–192 (ethyl acetate) |
| (e) | 9-{3-[4-(2-Phenyl-propionamido)-piperidino]-propyl-}-adenine from 9-[3-(4-amino-piperidino)-propyl]adenine and 2-phenyl-propionic acid chloride | 27 | 185–187 (ethyl acetate) |
| (f) | 9-{3-[4-(Furan-2-carbonylamido)-piperidino]-propyol}-adenine from 9-[3-(4-amino-piperidino)-propyl]-adenine and furan-2-carboxylic acid chloride | 39 | 201–202 (isopropanol) |
| (g) | 9-{3-[4-(Thiophene-2-carbonyl-amido)-piperidino]-propyl}-adenine from 9-[3-(4-amino-piperidino)-propyl]-adenine and thiophene-2-carboxylic acid chloride | 55 | 210–212 (isopropanol) |
| (h) | 9-{3-[4-(pyridine-3-carbonylamido)-piperidino]-propyl}-adenine from 9-[3-(4-amino-piperidino)-propyl]-adenine and 3-(isobutoxy-carbonyloxycarbonyl)-pyridine | 29 | 203–205 (isopropanol/diethyl ether) |
| (i) | 9-{3-[4-(4-Aminocarbonyl-benz-amido)-piperidino]-propyl}-adenine from 9-[3-(4-amino-piperidino)-propyl]-adenine and 4-(isobutoxycarbonyloxycarbonyl)-benzamide | 39 | 278–280 (acetone) |
| (j) | 9-[3-(4-Benzenesulphonamido-piperidino)-propyl]-adenine from 9-[3-(4-amino-piperidino)-propyl]-adenine and benzene-sulphochloride | 23 | 175–177 (ethyl acetate) |
| (k) | 9-[3-(4-Pivaloylamido-piperidino)-propyl]-adenine from 9-[3-(4-amino-piperidino)-propyl]-adenine and pivalic acid chloride | 53 | 190–192 (isopropanol/ligroin) |
| (l) | 9-[3-(4-Cyclopropancarbonyl)-amido-piperidino)-propyl]-adenine from 9-[3-(4-amino-piperidino)-propyl]-adenine and cyclopropane carboxylic acid chloride | 27 | 202–204 (ethyl acetate) |
| (m) | 9-[3-(4-Cyclohexancarbonyl-amido-piperidino)-propyl]-adenine from 9-[3-(4-amino-piperidino)-propyl]-adenine and cyclohexane carboxylic acid chloride | 36 | 231–233 (isopropanol/ligroin) |
| (n) | 9-{3-[4-(3-Phenyl-propionamido)-piperidino]-propyl}-adenine from 9-[3-(4-amino-piperidino)-propyl]-adenine and 3-phenyl-propionic acid chloride | 44 | 182–183 (ethyl acetate) |
| (o) | 9-{3-[4-(3,4-Dimethoxy-cinnamoylamido)-piperidino]-propyl}-adenine from 9-[3-(4-amino-piperidino)-propyl]-adenine and 3,4-dimethoxy-cinnamic acid chloride | 29 | 218–219 (isopropanol) |

EXAMPLE 5

9-{3-[4-(4-Amino-benzamido)-piperidino]-propyl}-adenine

A mixture of 3.0 g. (0.007 mole) 9-{3-[4-(4-nitro-benzamido)-piperidino]-propyl}-adenine, 50 ml. methanol, 25 ml. tetrahydrofuran and 1 g. Raney nickel is hydrogenated for 2 hours at ambient temperature and 1 bar hydrogen pressure. The reaction mixture is thereafter filtered, the filtrate is evaporated and the residue is triturated with ethyl acetate. There are obtained 2.4 g. (86% of theory) 9-{3-[4-(4-aminobenzamido)-piperidino]-propyl}-adenine; m.p. 247°–248° C.

EXAMPLE 6

$N^6$-n-Butyl-9-[3-(4-benzamido-piperidino)-propyl]-adenine 50 ml. n-Butylamine are added to a solution of 12.0 g. (0.03 mole) 6-chloro-9-[3-(4-benzamido-piperidino)-propyl]-purine in 100 ml. n-propanol and the reaction mixture is heated under reflux for 6 hours. It is then evaporated in a vacuum and the residue is extracted with ethyl acetate. After evaporation of the solvent and recrystallization of the residue from isopropanol/diethyl ether, there are obtained 6.8 g. (52% of theory) $N^6$-butyl-9-[3-(4-benzamido-piperidino)-propyl]-adenine; m.p. 190°–192° C.

EXAMPLE 7

9-{3-[4-(4-t-Butylbenzamido)-piperidino]-propyl}-adenine hydrochloride

A suspension of 1.0 g. 9-{3-[4-(4-t-butylbenzamido)-piperidino]-propyl}-adenine in 10 ml. ethanol is mixed with excess ethereal hydrogen chloride solution. Upon mixing the solution with diethyl ether, there is obtained 0.95 g. (87% of theory) 9-{3-[4-(4-t-butylbenzamido)-piperidino]-propyl}-adenine hydrochloride; m.p. 285°–287° C.

The foregoing compounds can be used as such or they can be converted to salts with pharmacologically acceptable acids. They can be administered orally, as pills, tablets, capsules, powders and the like. The preferred form of oral administration is a tablet containing 10 to 300 mg of active compound.

The compounds can also be administered parenterally. Injection solutions containing 50 mg/ml of injection solution are preferred.

With respect to the proper dosage and methods of application for the instant compounds, these are comparable to those for the commercially known compound "Fragivix", i.e. 2-ethyl-3-(4′-hydroxybenzoyl)-benzofuran. The instant compounds make possible comprehensive therapy of acute as well as chronic phlebological and capillary afflictions as well as varicose syndromes.

The instant compounds retard reactions leading to edemas and swellings, including those of allergic origin.

The typical daily dosage of 10 to 300 mg results in reducing or eliminating the above afflictions, commonly within some days. A preferred dosage is 30–100 mg.

EXAMPLE 8

Preparation of pharmaceutical compositions

Composition 25 g active material according to the present invention
- 150 g lactose
- 100 g polyvinylpyrrolidone solution (5% in water)
- 5 magnesium stearate
- 15 g sodium amylopectin glycolate The active material is carefully mixed with the lactose in a kneader, thoroughly moistened with the polyvinylpyrrolidone solution and the resultant mass is forced through a sieve with a mesh size of 1.9 mm. The resulting granules are dried and freed from coarse components by passing through a sieve with a mesh size of 1.2 mm and from fines by means of a sieve with a mesh size of 0.6 mm.

These granules can be used directly for filling hard gelatin capsules (180 mg/capsule) and administered.

Furthermore, the granules can be mixed with the magnesium stearate and the sodium amylopectin glycolate and pressed into tablets. The diameter of the tablets is 8 mm, the weight 200 mg, the hardness 2.0 kg and the content of active material per tablet is 25 mg.

The superior activity of the novel compounds is shown by comparing the inhibition of the passive cutaneous anaphylactic reaction in rats produced by injection of serum containing reaginic antibodies to egg albumin. Diethylcarbamazin, i.e. 1-diethylcarbamoyl-4-methylpiperazine, was used as a comparison compound. Specifically, tests were run as follows:

Serum containing reaginic (IgE-like) antibody to egg albumin was prepared by injecting rats intramuscularly with 0.1 ml of a solution of the antigen (10 mg/ml) in saline together with 0.5 ml of Bordetella pertussis vaccine (Behring; $2 \times 10^{10}$ organisms/ml). 9–14 Days later the animals were bled from the abdominal aorta; the serum was pooled and stored at $-20°$ C. until required. The titer of the serum, i.e. the highest dilution inducing passive cutaneous anaphylaxis (PCA) in the rat following a 48-hour latent period, was between 1:8 and 1:32. For use in these experiments the serum was diluted 1:24. The reaginic nature of the antibody was demonstrated by its ability to induce PCA with a latent period in excess of 7 days and also by abolition of its PCA activity by heating it at 56° C. for 1 hour.

The animals were anesthetized with 2,2-dichloro-1,1-difluoroethyl-methyl ether, sold under the trademark Penthrane, and were sensitized by injecting 0.1 ml of the antiserum into the shaved abdominal flanks. After 48 hours for reaginic PCA, the animals were given an intravenous injection of 1 ml of saline solution containing 0.5% by weight of egg albumin and 0.25% by weight of Evans Blue.

After having killed and exsanguinated the animals, the size in square millimeters and the intensity, in arbitary scores, of the resulting blue spot were determined. The product of these two parameters was used to determine the degree of the reaction and the degree of reaction with no active material was taken as the standard against which to measure % inhibition of the anaphylactic reaction.

6 Animals were used per dose level and for control.

The test material was injected intravenously immediately before the antigen, using a solution in water containing 0.5% HCl and 2% of dimethylformamide. For comparative purposes there was also tested diethylcarbamoyl-4-methylpiperazine sold under the tradename Diethylcarbamazin. The volumes of the injections were varied to give the indicated dosage of the active material. The results obtained were as follows:

PCA Reaction in Rats Induced by Reaginic Antibodies (Ovalbumin 2×cryst, and Bord. pertussis $2 \times 10^{10}$) Active material applied intravenously immediately before antigen.

Table III

| Active Material | mg/kg | % Inhibition PCA |
|---|---|---|
| Diethylcarbamazin | 60.0 | 58 |
| Example 2b | 1.5 | 65 |
| Example 2e | 1.5 | 39 |
| Example 2f | 1.5 | 74 |
| Example 2j | 0.75 | 44 |
| Example 2k | 0.75 | 41 |
| Example 2l | 1.5 | 43 |
| Example 2m | 1.5 | 36 |
| Example 4a | 1.5 | 80 |
| Example 4d | 1.5 | 30 |
| Example 4f | 1.5 | 44 |

The present invention also provides pharmaceutical compositions which contain at least one of the new compounds in admixture with a solid or liquid pharmaceutical diluent or carrier and, if desired, also with odoriferous, flavoring and/or coloring materials, followed by forming into, for example, tablets or dragees or, with the addition of appropriate adjuvants, suspended or dissolved in water or oil, for example olive oil.

It will be understood that the specification and examples are illustrative but not limitative of the present invention and that other embodiments within the spirit and scope of the invention will suggest themselves to those skilled in the art.

What is claimed is:

1. A 9-[3-(4-amino-piperidino)-propyl]-adenine of the formula

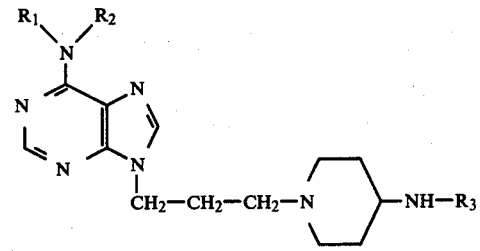

wherein
- $R_1$ is a hydrogen atom or a lower alkyl radical,
- $R_2$ is a hydrogen atom, an aryl radical, a lower alkyl radical, a hydroxy lower alkyl radical, or together with $R_1$ and the nitrogen atom to which they are attached form a tetramethyleneimino, pentamethyleneimino or hexamethyleneimino ring, and
- $R_3$ is a hydrogen atom or an acyl radical, or a salt thereof with a pharmacologically acceptable acid.

2. A compound or salt according to claim 1, wherein $R_1$ is a hydrogen atom or an alkyl radical with up to 4 carbon atoms, $R_2$ is a hydrogen atom, a phenyl radical, a naphthyl radical, an alkyl or hydroalkyl radical with up to 4 carbon atoms, or together with $R_1$ and the nitrogen atom to which they are attached form a tetramethyleneimino, pentamethyleneimino or hexamethyleneimino ring, and $R_3$ is a hydrogen atom; a lower alkanoyl radical optionally substituted by halogen atoms, a phenyl radical and/or a naphthyl radical; a lower alkenoyl radical substituted by a phenyl or naphthyl radical; a $C_{3-7}$-cycloalkylcarbonyl, benzoyl, furanecarbonyl, thiophenecarbonyl or pyridinecarbonyl radical optionally substituted by halogen atoms, or a hydroxyl, lower alkyl, lower alkoxy, lower alkoxycarbonyl, lower acyloxy, carboxyl, nitro, amino, cyano, trifluoromethyl, carbamoyl or benzyl radical; or a benzene sulphonic or methylsulphonic acid radical.

3. A compound or salt according to claim 1, wherein such compound is 9-{3-[4-(4-fluorobenzamido)-piperidino]-propyl}-adenine of the formula

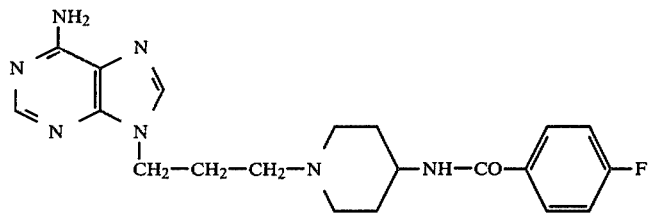

4. A compound or salt according to claim 1, wherein such compound is 9-{3-[4-(4-methylbenzamido)-piperidino]-propyl}-adenine of the formula

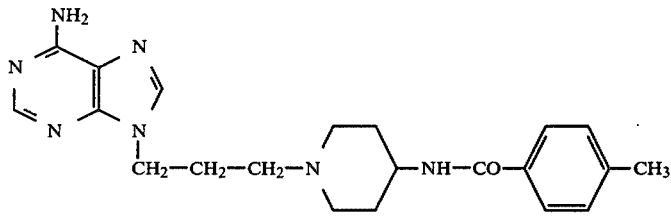

5. A compound or salt according to claim 1, wherein such compound is $N^6$-(2-hydroxethyl)-9-[3-(4-benzamido-piperidino)-propyl]-adenine of the formula

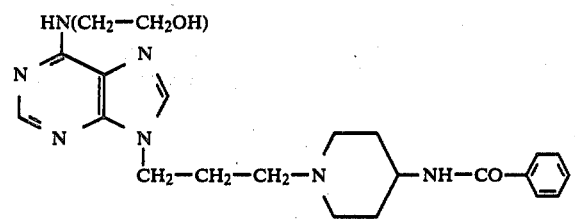

6. A compound or salt according to claim 1, wherein such compound is $N^6$-n-butyl-9-[3-(4-benazmido-piperidino)-propyl]-adenine of the formula

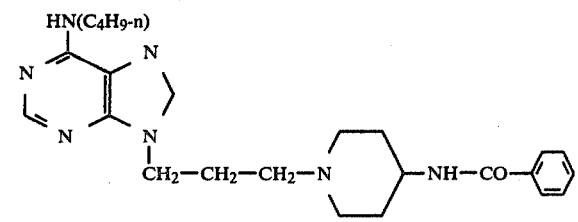

7. A compound or salt according to claim 1, wherein such compound is 9{-3-[4-(4-chlorobenzamido)-piperidino]-propyl}-adenine of the formula

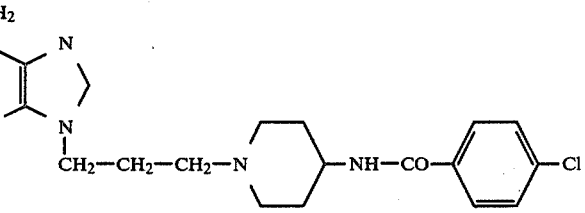

8. A composition comprising an anti-allergic, anti-inflammatory and anti-oedematous effective amount of an adenine according to claim 1, in admixture with a pharmacologically compatible diluent.

9. A method of diminishing an allergic condition in a patient which comprises administering to such patient an anti-allergically effective amount of a compound according to claim 1.

10. The method of claim 9, wherein such compound is
9-{3-[4-(4-fluorobenzamido)-piperidino]-propyl}-adenine,
9-{3-[4-(4methylbenzamido)-piperidino]-propyl}-adenine,
$N^6$-(2-hydroxyethyl)-9-[3-(4-benzamido-piperidino)-propyl]-adenine,
$N^6$-n-butyl-9-[3-(4-benzamido-piperidino)-propyl]-adenine, or
9-{3-[4-(4-chlorobenzamido)-piperidino]propyl}-adenine.

11. A method of diminishing an inflammatory condition in a patient which comprises administering to such patient an anti-inflammatory effective amount of a compound according to claim 1.

12. A method of diminishing an oedematous condition in a patient which comprises administering to such patient an anti-oedematally effective amount of a compound according to claim 1.

13. A compound or salt according to claim 1, wherein $R_3$ is a hydrogen atom.

14. A compound or salt according to claim 1, wherein $R_3$ is a benzoyl radical optionally substituted by halogen atoms, or a hydroxyl, lower alkyl, lower alkoxy, lower alkoxycarbonyl, lower acyloxy, carboxyl, nitro, amino, cyano, trifluoromethyl, carbamoyl or benzyl radical.

* * * * *

UNITED STATES PATENT AND TRADEMARK OFFICE
CERTIFICATE OF CORRECTION

PATENT NO. : 4,212,866
DATED : Jul. 15, 1980
INVENTOR(S) : Walter-Gunar Friebe et al It is certified that error appears in the above–identified patent and that said Letters Patent are hereby corrected as shown below:

Title Page  Delete "2804168" and insert --2804416--.
Priority

Signed and Sealed this

Twenty-eighth Day of April 1981

[SEAL]

Attest:

RENE D. TEGTMEYER

Attesting Officer

Acting Commissioner of Patents and Trademarks